United States Patent
Borrero (10) Patent No.: US 6,799,695 B1
(45) Date of Patent: Oct. 5, 2004

(54) SANITARY NAPKIN DISPENSING DEVICE

(76) Inventor: Miguel Borrero, P.O. Box 91, Bethel, NY (US) 12720

( * ) Notice: Subject to any disclaimer, the term of this patent is extended or adjusted under 35 U.S.C. 154(b) by 119 days.

(21) Appl. No.: 10/114,090

(22) Filed: Apr. 2, 2002

(51) Int. Cl.$^7$ ................................................ B65H 1/08
(52) U.S. Cl. ........................... 221/59; 221/61; 221/45; 221/279; 221/281; 206/467; 312/25
(58) Field of Search .......................... 221/279, 45, 59, 221/61, 102, 281, 282, 283, 303; 211/71; 312/35; 206/467

(56) References Cited

U.S. PATENT DOCUMENTS

| | | | | |
|---|---|---|---|---|
| 2,295,313 A | * | 9/1942 | Weir | 221/92 |
| 2,301,893 A | * | 10/1942 | Lifshey | 221/130 |
| 3,019,940 A | * | 2/1962 | Sutton | 221/48 |
| 3,860,304 A | * | 1/1975 | Bolton | 312/71 |
| 3,907,159 A | * | 9/1975 | Halm | 221/23 |
| 4,236,637 A | * | 12/1980 | Castner, Sr. et al. | 206/467 |
| 4,750,640 A | * | 6/1988 | Kobeck et al. | 221/186 |
| 5,265,759 A | * | 11/1993 | Coffin | 221/123 |
| 5,562,328 A | * | 10/1996 | Schottenfeld | 312/35 |
| 5,713,488 A | * | 2/1998 | Farrugia | 221/45 |
| 6,073,899 A | * | 6/2000 | Omrani | 248/311.2 |

* cited by examiner

*Primary Examiner*—Donald P. Walsh
*Assistant Examiner*—Michael E Butler
(74) *Attorney, Agent, or Firm*—Michael I Kroll (57) ABSTRACT

A dispensing device is provided for sanitary napkins of various shapes and sizes. The device is conveniently and efficiently packaged for optimal placement and utility within the private facilities of a home. The device includes a hinged lid allowing ready placement of the sanitary napkins within the device housing. When closed, a latch secures the lid. On one or more sides of the housing, a door is provided near the bottom that allows the user to retrieve a sanitary napkin from the bottom of the housing. The door or doors are hinged with a spring providing a bias to the closed position. Attached to the lid is a spring, the spring having an attached compression plate. When the lid is closed, the spring forces the compression plate against the sanitary napkins within the housing, thus maintaining the sanitary napkins in the proper position and orientation for grasping by the user, through the door. Hooks are provided to support a disposal bag. The device has mounting brackets and other attachment provisions for attaching the device to a wall. The device can also be used in a freestanding position without mounting.

1 Claim, 10 Drawing Sheets

SANITARY NAPKIN DISPENSING DEVICE

GROUND OF THE INVENTION

1. Field of the Invention

The present invention relates generally to a dispensing device and, more specifically, to a dispensing device for sanitary napkins.

2. Description of the Prior Art

There are numerous sanitary napkin holding and dispensing devices having selective storing and dispensing means. While these sanitary napkin holding and dispensing devices may be suitable for the purpose for which they were designed, they would not be as suitable for the purposes of the present invention as heretofore described.

It is thus desirable to provide a sanitary napkin dispensing device that may house a stack of various sized sanitary napkins. It is further desirable to provide a sanitary napkin dispensing device that may be selectively mounted to a wall or surface of choice. It is furthermore desirable to provide a sanitary napkin dispensing device that may be composed from a lightweight yet sturdy material.

SUMMARY OF THE PRESENT INVENTION

A primary object of the present invention is to provide a sanitary napkin dispensing device that may house a number of variously sized sanitary napkins.

Another object of the present invention is to provide a sanitary napkin dispensing device that may be selectively mounted to a convenient location of Yet another object of the present invention is to provide a sanitary napkins dispensing device that is inexpensive.

Still yet another object of the present invention is to provide a sanitary napkin dispensing device that may be selectively refilled.

Yet another object of the present invention is to provide a sanitary napkins dispensing device that may have it own waste containment element.

The sanitary napkins dispensing device includes a main housing, a refill lid, a refill lid latch, a spring element, a spring compression plate, a plastic bag hook and a sanitary napkin protective door.

The main housing is a modified-boxed shaped structure having a selectively opened end furnished therein. Also the main housing's selectively opened end provides the means for the selective refilling of the sanitary napkin dispensing device via the refill lid. The main housing provides the housing means for all of the intricate components that comprise the sanitary napkin dispensing device.

The main housing is furnished with a rectangular shaped aperture located at the base of its front most end. The main housing's selectively shaped aperture provides the dispensing means of the sanitary napkins dispensing device by allowing for a sanitary napkin to be selectively removed from the main housing.

The main housing element is further furnished with wall mounting brackets located at the top most ends of the sides of the sanitary napkin dispensing device. The refill lid is a rectangular shape structure that may be selectively attached to the main housing via a hinged element. The refill lid provides the user of the invention with the means to selectively refill the contents stored therein. The refill lid is furnished with a refill lid latch. The refill lid latch provides the retaining means for the sanitary napkins held within the main housing at time of use.

Also, the refill lid latch may resemble that of any conventional latching device found in industry and that is best fitted to perform the function. The refill lid latch works in conjunction with a refill latch mating element found on the main housing.

The refill lid is also coupled to a spring element. The spring element resembles that of a conventional manufacture spring element. Also, the spring element is coupled to the refill lid at one of its distal ends, while coupled to a rectangular-shaped compression plate attached at its other distal end. The spring element provides the sanitary napkin dispensing device with the linear force needed to compress a stack of sanitary napkins within the confines of the main housing.

The plastic bag hooks are cylindrical J-shaped hooked structures. The plastic bag hooks are located one at each of the side most ends of the bottom end of the main housing. The plastic bag hooks provides the means for the user to selectively engage and retain a plastic bag on the sanitary napkin dispensing device for the collection of sanitary napkins waste material.

The sanitary napkin protective door is a rectangular shaped structure. The sanitary napkin protective door is designed to fit into and work in conjunction with the rectangular shaped aperture of the main housing. The sanitary napkin protective door provides the user of the invention with access and protective means for the next sanitary napkin in the main housing as it is dispensed for use.

Also, the sanitary napkin protective door is coupled to a spring-loaded hinge device in order to be automatically returned to the closed position to produce its protective qualities.

An individual having a sanitary napkin dispensing device selectively attached to a wall or other convenient location may access and remove a sanitary napkin for use. The individual upon using the sanitary napkin may then discard the wrapping and waste material into the plastic bag that is selectively attached to the plastic bag hooks. The individual may repeat this process as it seems fit or until it is such time to refill the contents within the sanitary napkin dispensing device.

The present invention includes a sanitary napkin dispenser, comprising: a housing, the housing having a front side, bottom side, left side, right side, and a lid, the lid being movable from a closed to an open position such that sanitary napkins can be placed within the housing, the housing having a door proximate the housing bottom side, the door being movable between an open and closed position, the door being sized to allow passage of one of the sanitary napkins; a spring, the spring being attached to the lid, the spring being disposed within the housing when the lid is closed; and a compression plate, the compression plate being attached to the spring and positioned such that the spring is compressed when sanitary napkins are in the housing.

The present invention includes a sanitary napkin dispenser, comprising housing means for storing sanitary napkins; means for placing the sanitary napkins within the housing means; means for biasing a horizontally oriented plate against the stored sanitary napkins; and means for accessing the sanitary napkins and removing such sanitary napkin from the housing means. The present invention also comprises means for hanging objects from the housing.

Additional objects of the present invention will appear as the description proceeds.

The present invention overcomes the shortcomings of the prior art by providing a sanitary napkins dispensing device that is convenient to the user, inconspicuous rounding environment, affordable, and that works in conjunction with already manufactured sanitary napkins.

The foregoing and other objects and advantages will appear from the description to follow. In the description reference is made to the accompanying drawing, which forms a part hereof, and in which is shown by way of illustration specific embodiments in which the invention may be practiced. These embodiments will be described in sufficient detail to enable those skilled in the art to practice the invention, and it is to be understood that other embodiments may be utilized and that structural changes may be made without departing from the scope of the invention. In the accompanying drawing, like reference characters designate the same or similar parts throughout the several views.

The following detailed description is, therefore, not to be taken in a limiting sense, and the scope of the present invention is best defined by the appended claims.

BRIEF DESCRIPTION OF THE DRAWING FIGURES

In order that the invention may be more fully understood, it will now be described, by way of example, with reference to the accompanying drawing in which.

DESCRIPTION OF THE REFERENCED NUMERALS

Turning now descriptively to the drawings, in which similar reference characters denote similar elements throughout the several views, the figures illustrate the Sanitary Napkin Dispensing Device of the present invention. With regard to the reference numerals used, the following numbering is used throughout the various drawing figures.
10 Sanitary Napkin Dispensing Device of the present invention
12 sanitary napkin
14 disposal bag
16 wall
18 user's hand
20 housing
22 housing front side
24 housing left side
26 housing right side
28 housing bottom side
30 housing rear side
32 lid
34 lid hinge
36 lid latch
38 lid latch knob
40 front side interior groove
42 spring
44 compression plate
46 door
48 front side access hole
50 door spring
52 disposal bag hooks
54 mounting brackets

DETAILED DESCRIPTION OF THE PREFERRED EMBODIMENT

Turning now descriptively to the drawings, in which similar reference characters denote similar elements throughout the several views, FIGS. 1–9 illustrate the Sanitary Napkin Dispensing Device of the present invention indicated generally by the numeral 10.

Figure 1:
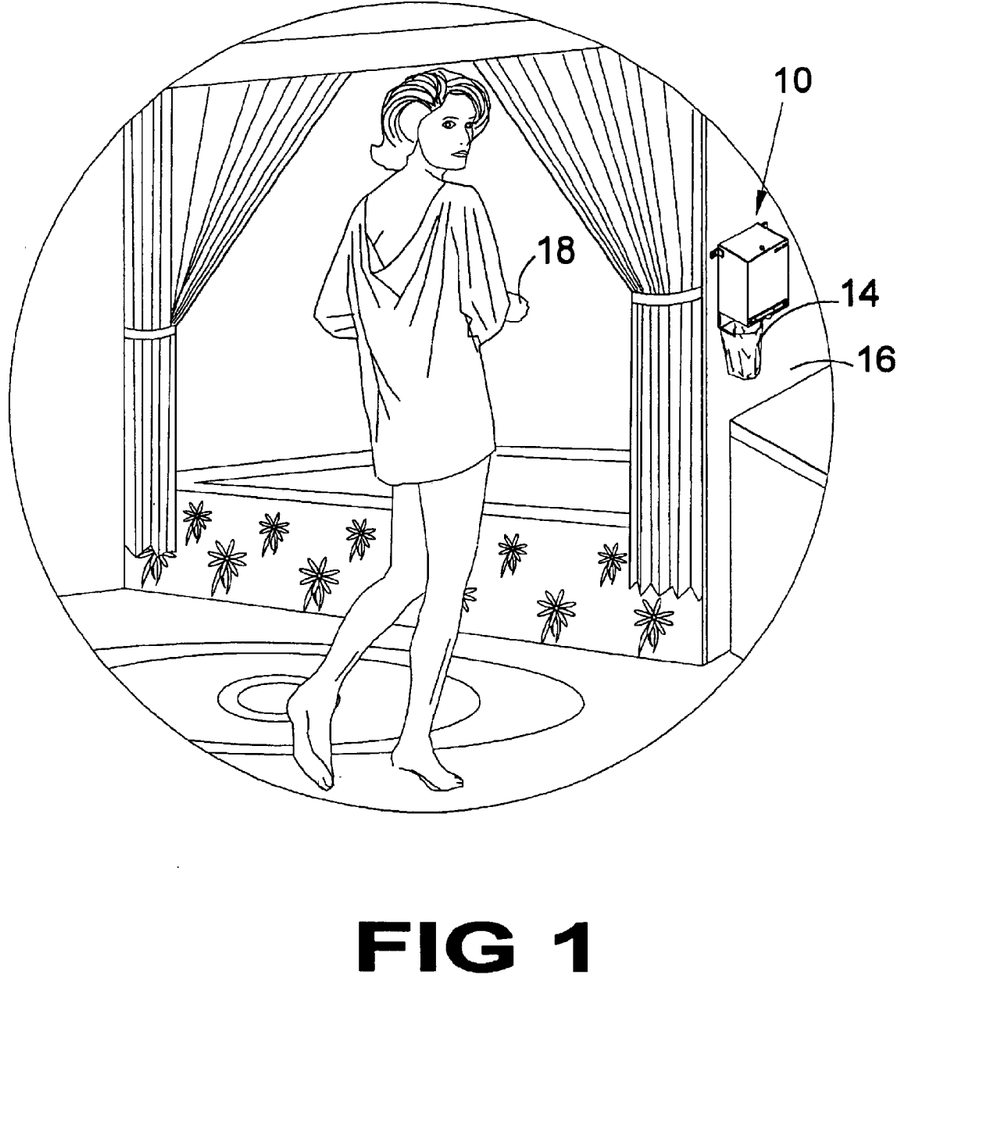
FIG. 1 is perspective view of the present invention. Shown is an individual in the private vicinity obtaining a sanitary napkin from the sanitary napkin dispensing device. Also shown is the sanitary napkin dispensing device selectively mounted waist high on one of the walls that comprise the private vicinity. Shown also is a sanitary dispensing device having a disposable plastic bag selectively attached to the plastic bag hooks of the device.
Figure 2:
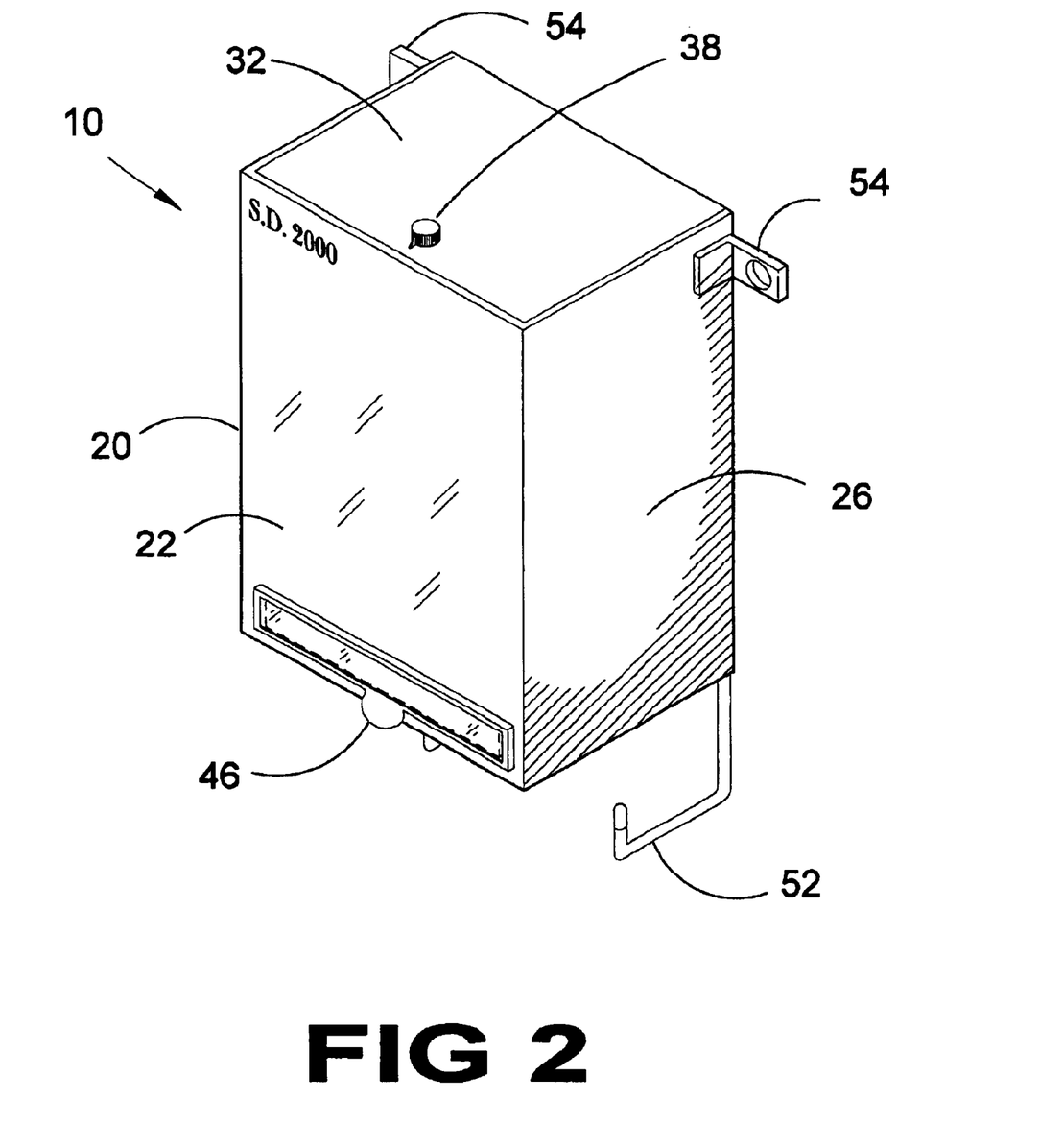
FIG. 2 is a perspective view. Shown are the linear displacement relations of several of the intricate components that comprise the sanitary napkin dispensing device.

The device 10 is shown in use in FIG. 1. As shown in FIGS. 1–9, the device 10 encloses sanitary napkins 12, supports a disposal bag 14, and can be mounted on a wall 16. Access to the sanitary napkins 12 is by hand 18. The device has a housing 20 that has a front side 22, left side 24, right side 26, bottom side 28 and rear side 30. The housing 20 is sized to store a sizable number of sanitary napkins 12. When such napkins 12 are substantially planar, the housing 20 is sized to allow the napkins 12 to be stacked in a generally horizontal orientation.

Figure 3:
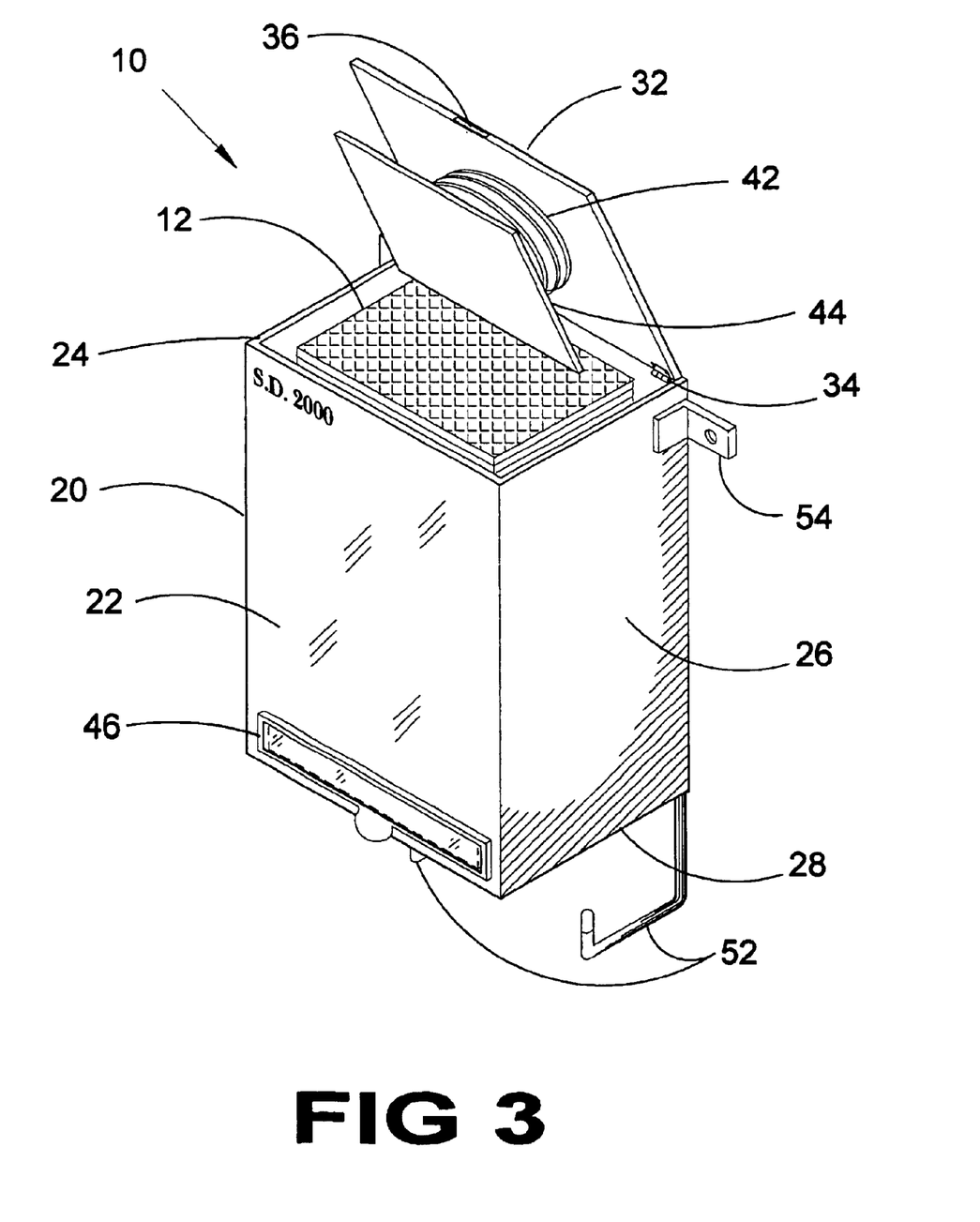
FIG. 3 is a perspective view, shown is the sanitary napkin dispensing device with its refill lid ajar to illustrate the opening action of the refill lid. Also shown is the spring and spring compression plate as they are affixed to the bottom side of the refill lid. Shown also is the sanitary napkin dispensing device topped off with a stack of sanitary napkins.

As shown in FIG. 3, a lid 32 is provided for access to the housing 20 such that sanitary napkins 12 may be placed within. A lid hinge 34 secures the lid 32 to the housing rear side 30. A lid latch 36 is secured to the lid 32, and is rotatable within the lid by turning the lid latch knob 38. In the latched position the lid latch 36 extends from within the lid 32 and into a groove 40 on the inside of the housing front side 22, thus preventing the lid 32 from being opened. By rotating the lid latch knob 38, the lid latch 36 clears the groove 40, allowing the lid 32 to be opened about lid hinge 34.

In the preferred embodiment, the housing 20 and lid 32 is constructed from plastic, although aluminum, stainless steel, wood, and other materials may also be used, all in accordance with the present invention, and as determined by the intended end use for the overall device 10, as will occur to those of skill in the art upon review of the present disclosure.

As shown in FIG. 3 and FIGS. 6–9, a spring 42 is attached to the lid 32 and disposed within the housing 20, when the lid 32 is closed. Attached to the spring is a generally planar compression plate 44, positioned to be generally parallel to housing bottom side 28 when the lid 32 is closed. The spring 42 is compressed as the lid 32 is closed and the compression plate 44 bears upon the sanitary napkins 12. This pressure assures the proper orientation and positioning of the sanitary napkins 12 within the housing 20. The pressure is maintained as each sanitary napkin 12 is removed. After the final sanitary napkin 12 is removed, the compression plate 44 is substantially flush with the housing bottom side 28.

In the preferred embodiment, the spring 42 and compression plate 44 are constructed from plastic, although other materials, such as aluminum and stainless steel can also be used, all in accordance with the present invention, and as determined by the intended end use for the overall device 10, as will occur to those of skill in the art upon review of the present disclosure.

Figure 4:
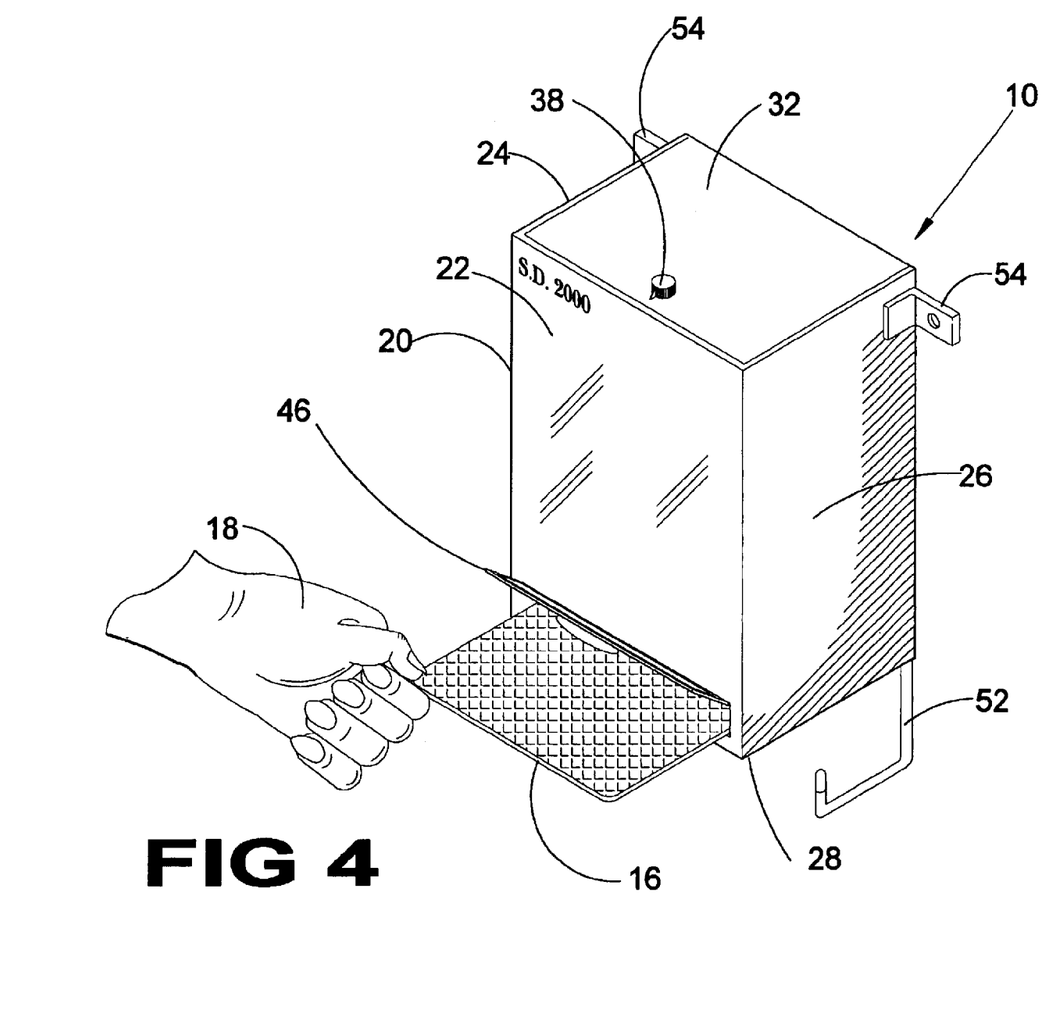
FIG. 4 is a perspective view. Shown is the hand of an individual as it extracts a sanitary napkin form the protective access door of the invention. Also shown is the sanitary napkin dispensing device as it performs its ideal functioning aspect. Shown also is the functioning aspect of the protective access door.
Figure 7:
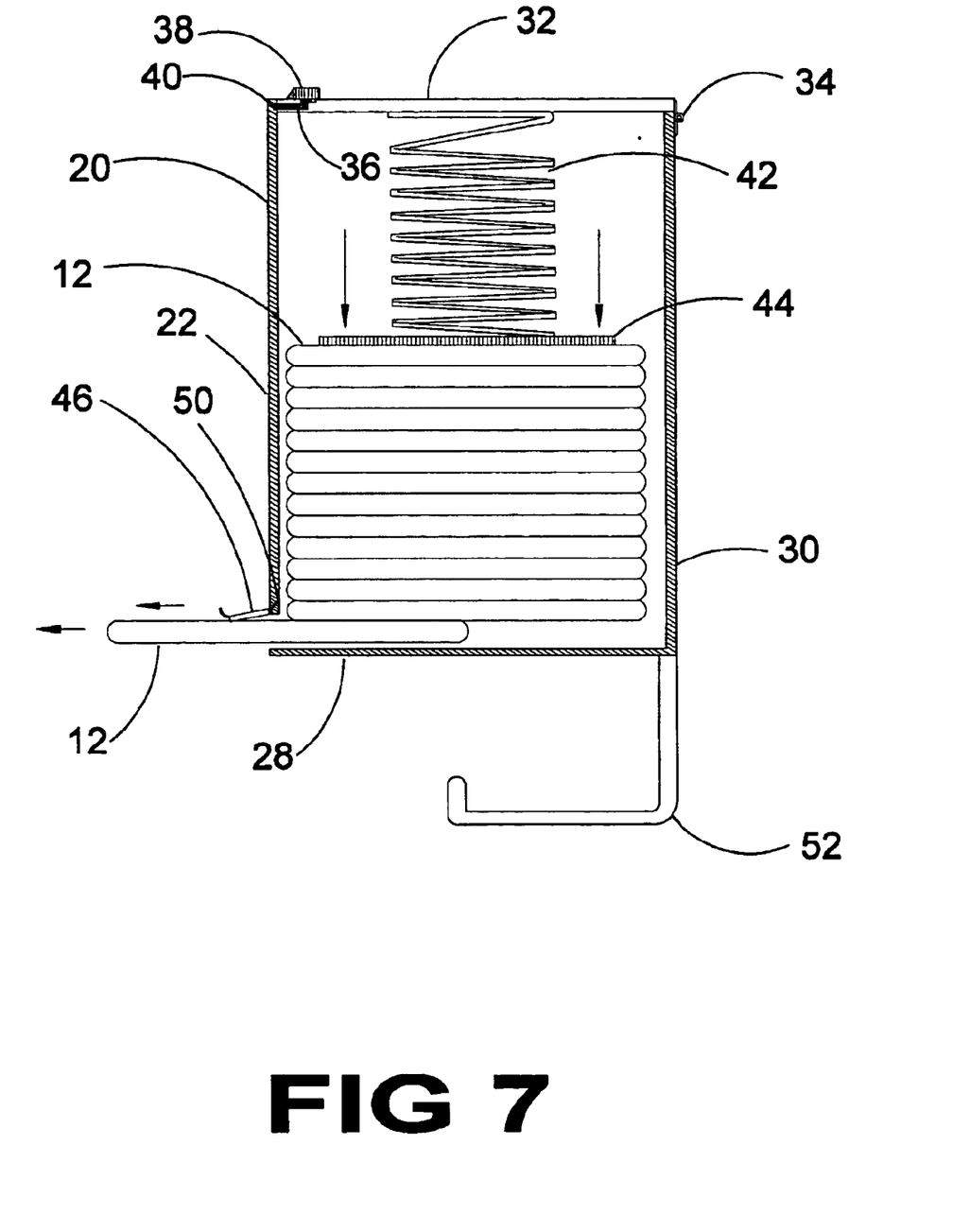
FIG. 7 is a sectional view showing the function aspect of the spring and spring compression plate. Also shown is the spring and spring compression plate as they relate to the stack of sanitary napkins encased in the sanitary napkin dispensing device. Shown also is the functioning aspect of the protective door. Shown also is the protective door as it relates to a sanitary napkin as it is pulled through the protective door of the sanitary napkin dispensing device.
Figure 8:
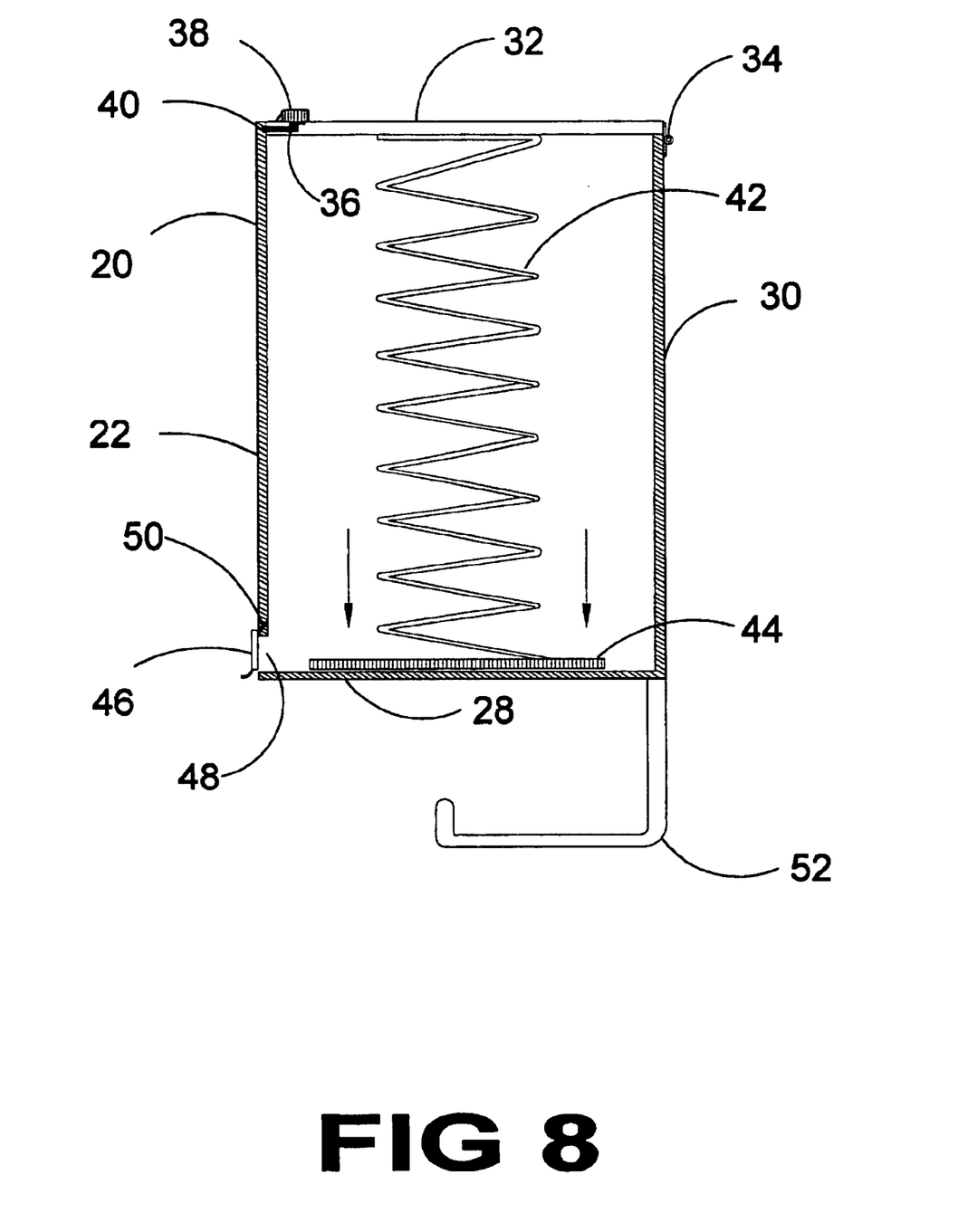
FIG. 8 is a sectional view. Shown is the spring fully extended. Also shown is the empty sanitary napkin dispensing device with the compression plate seated flush against the bottom most section of the inner wall of the sanitary napkin dispensing device.
Figure 9:
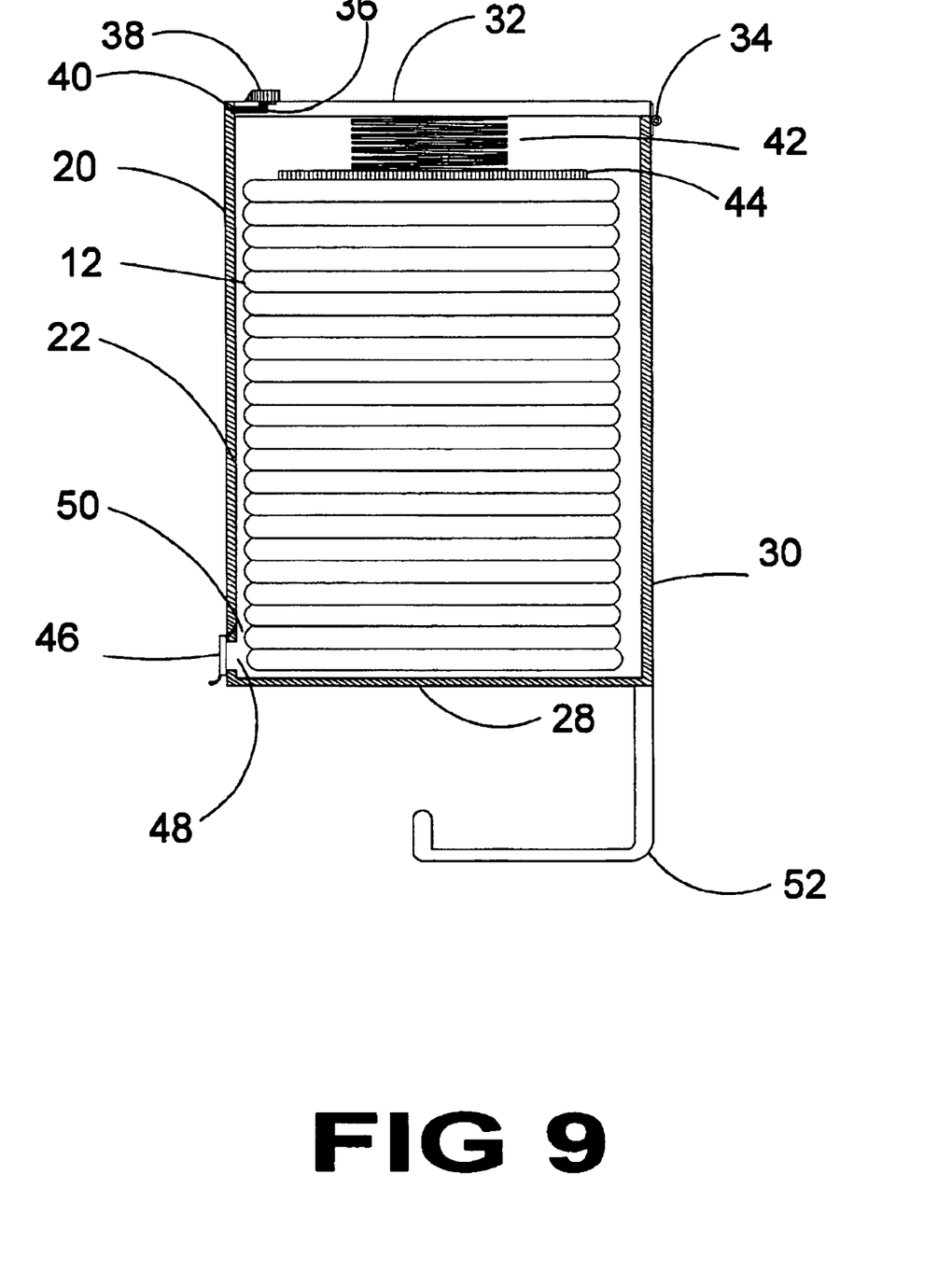
FIG. 9 is a sectional view, showing the spring in the fully compressed position. Also shown is the sanitary napkin dispensing device filled with a stack of sanitary napkins.

A door 46 is provided that opens to expose a housing front side access hole 48. As shown in FIG. 4 and FIG. 7, the access hole 48 is proximate the housing bottom side 28, such that hand 18 access is provided for removing a sanitary napkin 12 from the bottom of the housing 20. The access hole 48 is further sized such that the sanitary napkin 12 can be removed without folding or deformation.

Figure 6:
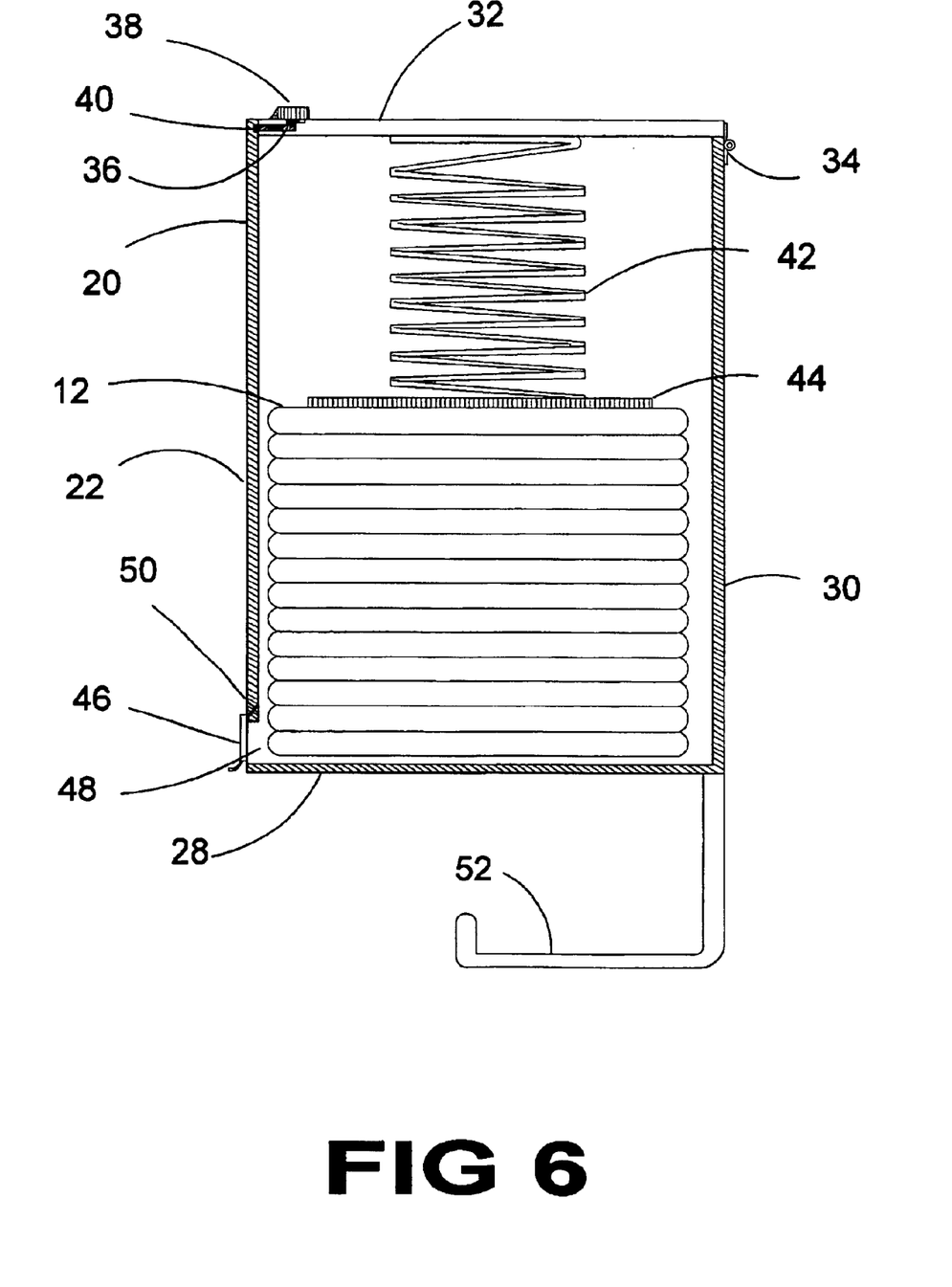
FIG. 6 is a sectional view showing the inner housing of the main housing of the invention. Also shown is the sanitary napkin dispensing device selectively retaining a stack of sanitary napkins. Shown also is the spring and spring compression plate as they work in conjunction to compresses a stack of sanitary napkins that are housed in the sanitary napkin dispensing device.

As shown in FIG. 6, the door 46 is biased to the closed position by a small spring 50. This assures that the housing 20 is sealed for sanitary purposes until access is desired.

In the preferred embodiment, the door 46 and access hole 48 are positioned on the housing front side 22. In other embodiments, the door 46 and access hole 48 are positioned on the housing left side 24 or the housing right side 26, or a combination of two or more of the front side 22, left side 24, and right side 26. This flexibility allows hand 18 access from a variety of angles, such angles often being dictated by the chosen place of positioning for the device 10.

Figure 5:
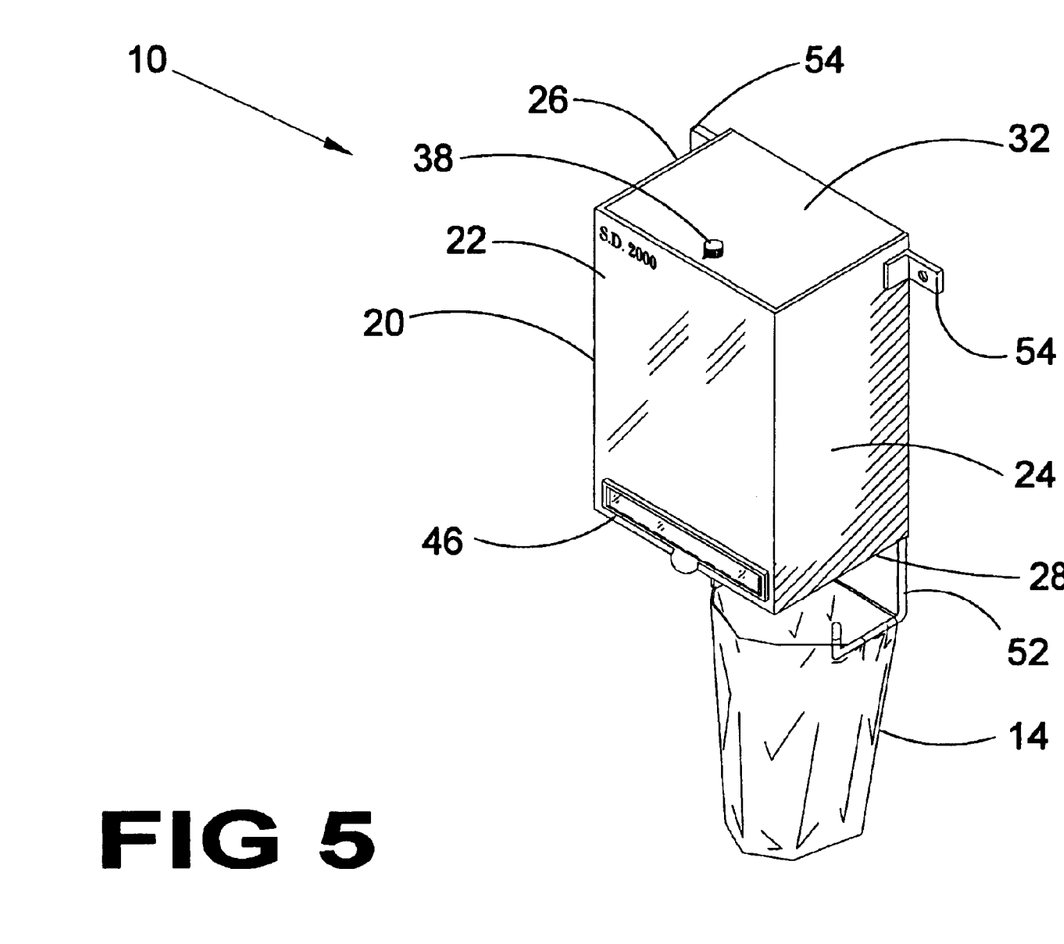
FIG. 5 is a perspective view. Shown is the selectively attachable plastic waste bag as it is attached to the plastic bag hook. Also shown is the sanitary napkin dispensing device in its entirety with all attachments and accessories.

In many instances it will be desirable to have a disposal bag 14 available in the proximity of the device 10, as shown in FIG. 1 and FIG. 5. For this reason, one or more hooks 52 are provided and attached to the housing bottom side 28, proximate the housing rear side 30. These hooks 52 can be positioned extend in the desired direction, thus optimizing the device 10 for a particular placement. In other embodiments (not shown), the hooks 52 are rotatable.

As shown in FIG. 1, it is often desirable to mount the device 10 on a wall 16. Mounting brackets 54 are provided for this purpose, and are attached to the housing left side 24 and right side 26. In other embodiments (not shown), other attachment means are provided such as housing rear side 30 slots, housing rear side 30 screw holes, and the like, all in accordance with the present invention, and as determined by the intended end use for the overall device 10, as will occur to those of skill in the art upon review of the present disclosure.

Figure 10:
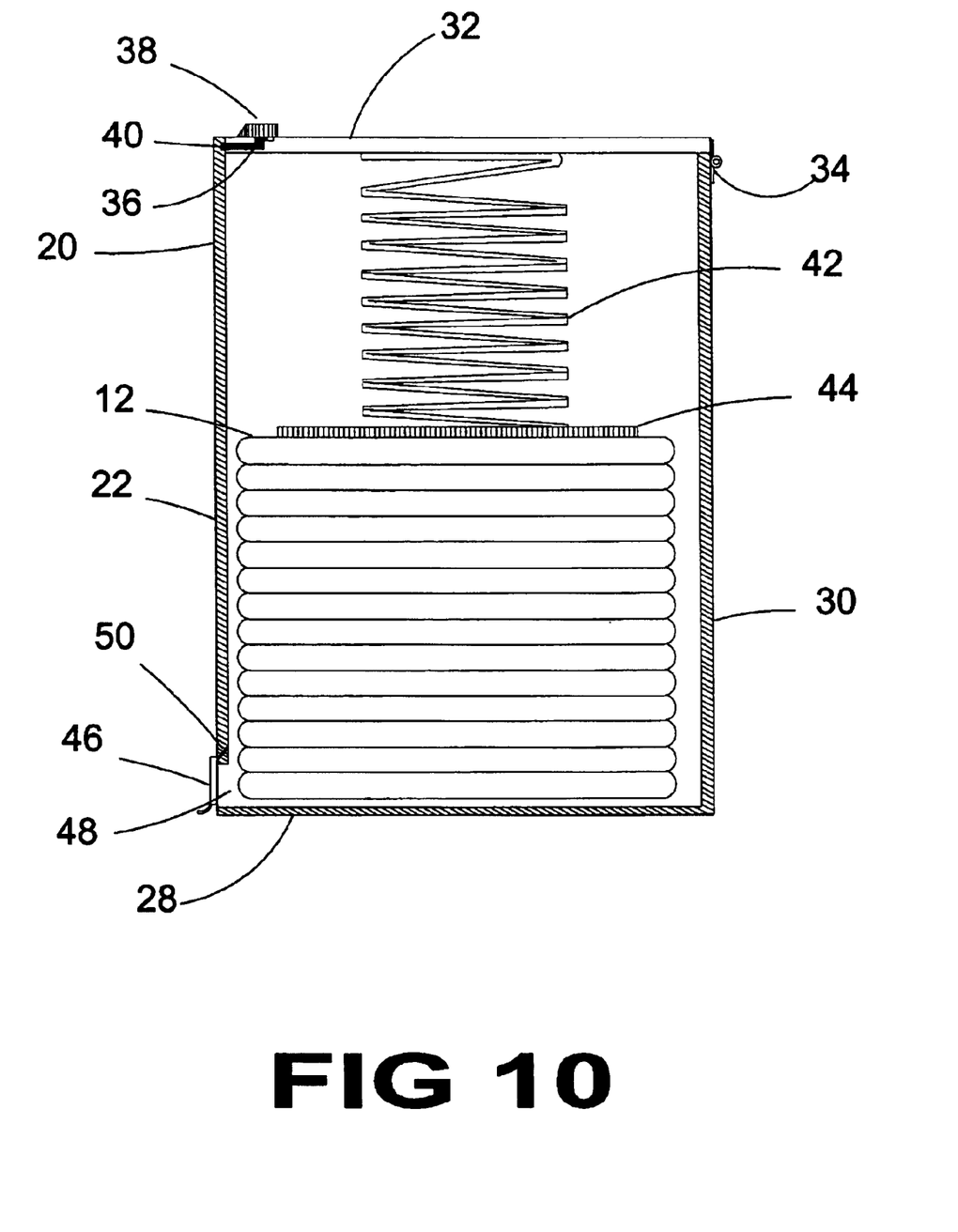
FIG. 10 is a sectional view, showing the freestanding embodiment.

In another embodiment, such as shown in FIG. 10, the hooks 54 are not present, or do not extend below the housing bottom side 28, allowing the housing bottom side 28 to serve as a base for a freestanding utilization of the device 10.

It will be understood that each of the elements described above, or two or more together may also find a useful application in other applications differing from that described above.

While certain novel features of this invention have been shown and described and are pointed out in the annexed claims, it is not intended to be limited to the details above, since it will be understood that various omissions, modifications, substitutions and changes in the forms and details of the device illustrated and in its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is:

1. A sanitary napkin dispenser consisting of:

a housing, the housing having a front side, a back side, bottom side, left side, right side, and a lid covering a top opening into said housing, the lid being movable from a closed to an open position such that sanitary napkins can be stacked horizontally within the housing, the housing having a door covering a front opening in said front side extending from the left side to the right side proximate the housing bottom side, the door being movable between an open and closed position, the door being sized to allow sliding passage of one of the sanitary napkins when said door is in its open position;

a spring, one end of the spring being attached to the lid, the spring being disposed within the housing when the lid is closed;

a compression plate, the compression plate being attached to a second end of the spring and positioned such that the spring is compressed when sanitary napkins are stacked in the housing;

said door being hinged along a top edge thereof to the front side of said housing above said door opening, and a spring biasing said door into its closed position;

said lid being hinged to a top edge of said back side and having a latch to secure said lid in its closed position, said latch having a rotatable knob to release said lid from its closed position;

a plurality of hooks attached to the bottom side of said housing for hanging plastic bags, one or more of said hooks being rotatable; and said housing rear side having at least one slot, the slot being sized to receive a screw head and allow the screw shaft to slide along the slot, such that the device may be secured to a wall in which the screw has placed.

* * * * *